United States Patent
Bouhnik et al.

(10) Patent No.: US 10,690,785 B2
(45) Date of Patent: Jun. 23, 2020

(54) SYSTEMS AND METHODS FOR NUCLEAR MEDICINE IMAGING USING SODIUM BASED CRYSTALS

(71) Applicant: General Electric Company, Schenectady, NY (US)

(72) Inventors: Jean-Paul Bouhnik, Zichron Yaacov (IL); Yaron Hefetz, Kibbutz Alonim (IL); Sharon Golden, Tirat Carmel (IL); Chang Lyong Kim, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/896,866

(22) Filed: Feb. 14, 2018

(65) Prior Publication Data
US 2019/0250285 A1    Aug. 15, 2019

(51) Int. Cl.
*G01T 1/20* (2006.01)
*A61B 6/00* (2006.01)
*G01T 1/202* (2006.01)
*G01T 1/164* (2006.01)
*A61B 6/03* (2006.01)

(52) U.S. Cl.
CPC .......... *G01T 1/2002* (2013.01); *A61B 6/4057* (2013.01); *A61B 6/4233* (2013.01); *G01T 1/164* (2013.01); *G01T 1/2018* (2013.01); *G01T 1/2023* (2013.01); *A61B 6/032* (2013.01); *A61B 6/037* (2013.01); *A61B 6/4266* (2013.01)

(58) Field of Classification Search
None
See application file for complete search history.

(56) References Cited

U.S. PATENT DOCUMENTS 5,091,650 A * 2/1992 Uchida ................. G01T 1/202
                                                       250/363.03
6,369,391 B1    4/2002 Hefetz et al.
6,576,907 B1    6/2003 Klein et al.
(Continued)

FOREIGN PATENT DOCUMENTS

EP    0221503 A2    5/1987
EP    0378896 A2    11/1988
(Continued)

OTHER PUBLICATIONS

Karp et al., "Performance of a Position-sensitive Scintillation Detector", The Institute of Physics, Jan. 29, 1985 (13 pages).

*Primary Examiner* — Edwin C Gunberg
(74) *Attorney, Agent, or Firm* — The Small Patent Law Group LLC; Dean D. Small (57) ABSTRACT

An imaging detector is provided that includes a continuous NaI crystal, a glass plate, an array of SiPMs, and an array of concentrators. The continuous NaI crystal defines a reception side and a detection side. The glass plate is disposed on the detection side of the continuous NaI crystal, and is interposed between the detection side of the continuous NaI crystal and the array. The array of concentrators corresponds to the array of SiPMs, and is interposed between the array of SiPMs and the glass plate. Each concentrator has a reception side opening that is larger than a detection side opening, with the detection side opening disposed proximate to a corresponding SiPM.

20 Claims, 7 Drawing Sheets

(56) References Cited

U.S. PATENT DOCUMENTS

| | | | |
|---|---|---|---|
| 7,592,596 B2 | 9/2009 | Klein et al. | |
| 8,350,219 B2 * | 1/2013 | Koren | G01T 1/20 250/362 |
| 2011/0017916 A1 * | 1/2011 | Schulz | G01T 1/202 250/368 |
| 2014/0339409 A1 * | 11/2014 | Stephenson | G01V 5/12 250/256 |

FOREIGN PATENT DOCUMENTS

| | | |
|---|---|---|
| EP | 0534683 A2 | 3/1993 |
| GB | 1529215 A | 10/1978 |
| SU | 01612764 A1 | 3/1993 |
| WO | 9213492 A | 8/1992 |

\* cited by examiner

SYSTEMS AND METHODS FOR NUCLEAR MEDICINE IMAGING USING SODIUM BASED CRYSTALS

BACKGROUND

The subject matter disclosed herein relates generally to medical imaging systems, and more particularly to radiation detection systems.

Photomultiplier tubes (PMTs) may be used in connection with imaging, such as nuclear medicine imaging. However, PMT based systems may not provide desired performance and/or may be cost prohibitive, particularly as the cost of PMTs increases. Similarly, solid state detectors (e.g., CZT) may present issues with respect to cost and/or performance.

BRIEF DESCRIPTION

In accordance with an embodiment, an imaging detector is provided that includes a continuous NaI crystal, a glass plate, an array of Geiger mode avalanche photodiodes or Silicon Photomultipliers (SiPMs), and an array of concentrators. The continuous NaI crystal defines a reception side and a detection side. The glass plate is disposed on the detection side of the continuous NaI crystal, and is interposed between the detection side of the continuous NaI crystal and the array. The array of concentrators corresponds to the array of SiPMs, and is interposed between the array of SiPMs and the glass plate. Each concentrator has a reception side opening that is larger than a detection side opening, with the detection side opening disposed proximate to a corresponding SiPM.

In accordance with another embodiment, an imaging system is provided that includes a continuous NaI crystal, a collimator, a glass plate, an array of SiPMs, an array of concentrators, and at least one processor. The continuous NaI crystal defines a reception side and a detection side. The collimator may be configured as a non-registered collimator, and is disposed on the reception side of the continuous NaI crystal. The glass plate is disposed on the detection side of the continuous NaI crystal, and is interposed between the detection side of the continuous NaI crystal and the array. The array of concentrators corresponds to the array of SiPMs, and is interposed between the array of SiPMs and the glass plate. Each concentrator has a reception side opening that is larger than a detection side opening, with the detection side opening disposed proximate to a corresponding SiPM. The at least one processor is operably coupled to the array of SiPMs, and is configured to acquire imaging information with the array of SiPMs, and to reconstruct an image using the imaging information.

In accordance with another embodiment, a method includes providing a continuous NaI crystal defining a reception side and a detection side. The method also includes disposing a glass plate on the detection side of the continuous NaI crystal. Further, the method includes disposing an array of SiPMs with the glass plate interposed between the detection side of the continuous NaI crystal and the array. Also, the method includes coupling an array of concentrators to the array of SiPMs, with the array of concentrators between the array of SiPMs and the glass plate. Each concentrator has a reception side opening that is larger than a detection side opening, with the detection side opening disposed proximate to a corresponding SiPM.

DETAILED DESCRIPTION

The foregoing summary, as well as the following detailed description of certain embodiments and claims, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide systems and methods for use of sodium based continuous crystals in connection with nuclear medicine (NM) imaging (e.g., use of a grooved NaI crystal in connection with light concentrators and SiPMs).

Various embodiments provide improved NM detection using a NaI scintillator in connection with SiPMs. In various embodiments, detectors are provided that have improved energy resolution, no energy tail, improved spatial resolution, improved depth of interaction within the crystal, no magnetic susceptibility, relatively small edge dead space, improved uniformity, and/or continuous detection properties (e.g., no need for registered collimation). Additionally or alternatively, various embodiments also provide good timing resolution, high count rate capability and coincidence capabilities (e.g., relative to the use of NaI scintillators in connection with PMT, or relative to the use of CZT detectors), along with relatively low cost. Generally speaking, various embodiments provide lower cost and improved performance relative to imaging system that use NaI scintillators in connection with PMT, or that use solid state (e.g., CZT) detectors.

Various embodiments provide increased quantum efficiency and/or improved light collection. While NaI crystals are used in certain embodiments, it may be noted that other crystals, such as LSO (LBS) may be used in various embodiments. LSO crystals may be thinner for the same stopping power as a comparable NaI crystal, and may have 75% light efficiency which may be compensated for by improved geometric and quantum efficiency. Use of a thinner crystal may provide better spatial resolution, while use of LSO instead of NaI can reduce or eliminate the need for sealing moisture out, reducing cost and dead space. Further, LSO crystals may be faster than NaI crystals, improving signal to noise ratio and increase count rate capability In addition, other scintillators, like GAGG, GFAG, T12LaC15 and SrI2, having close to or better light efficiency and higher density may be used.

Various embodiments also provide for the elimination of a registered collimator, improving stability and reducing cost. Further, SiPMs may be sized smaller than PMTs, improving spatial resolution and/or reducing the number of electronic channels.

A technical effect of at least one embodiment includes improved image quality. A technical effect of at least one embodiment includes reduced cost.

Figure 1:
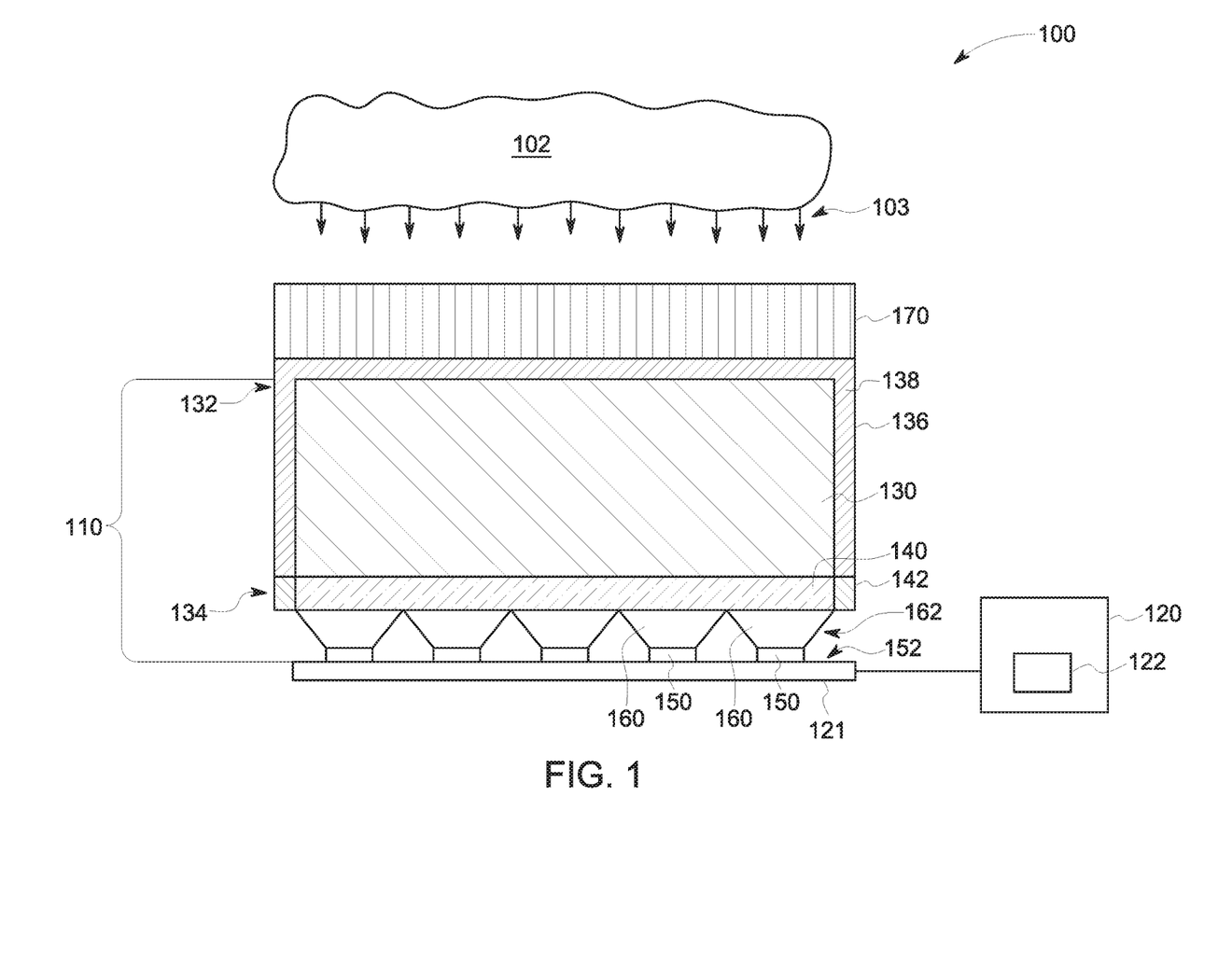
FIG. 1 provides a schematic side sectional view of an imaging system according to an embodiment.

FIG. 1 provides a schematic side sectional view of an imaging system 100. The imaging system includes an imaging detector 110, a processing unit 120, and a collimator 170. Generally, the imaging system 100 may be configured as a nuclear medicine (NM) imaging system that is configured to acquire emissions 103 (e.g., emissions due to an administered radiopharmaceutical) from an object 102 and to recreate an image of the object 102. The collimator 170 is configured to control or limit the angle at which photons impact the imaging detector 110, and the processing unit 120 is configured to acquire imaging information from the imaging detector 110 and to reconstruct an image of the object 102 using the acquired imaging information. It may be noted that while only a single detector and collimator, for example, are shown in FIG. 1 for ease of illustration, multiple different detector units each including a detector and collimator may be employed in various embodiments. For example, the imaging system 100 may be configured as a multi-head imaging system (see also FIG. 8 and related discussion), with plural detector units mounted to a gantry having a bore. Each detector unit may include an arm and a head, with the arm configured to articulate the head radially toward and/or away from a center of the bore of the gantry, and with the head including at least one detector, and configured to pivot about an end of the arm to provide a range of positions from which imaging information is acquired.

The depicted imaging detector 110 of the illustrated embodiment includes a continuous NaI crystal 130, a glass plate 140, an array 152 of SiPMs 150 (or avalanche photodiodes), and an array 162 of concentrators 160. Generally, the continuous NaI crystal 130 is configured to act as a scintillator, receiving emissions from the object 102 and, in response to the received emissions, generating light photons that are transmitted via the glass plate 140 to the concentrators 160. The concentrators 160 act to direct or funnel the generated light photons to the corresponding SiPMs 150. Responsive to the reception of light, the SiPMs generate signals which are acquired by the processing unit 120 and used to reconstruct an image.

As seen in FIG. 1, the depicted continuous NaI crystal 130 defines a reception side 132 and a detection side 134. The NaI crystal 130 is referred to herein as continuous as it has not been cut or separated into pixels, or is non-pixelated. Such a non-pixelated arrangement reduces costs in various embodiments. The reception side 132 is oriented toward the object 102 being imaged (or source of measured or detected radiation), while the detection side 134 is oriented toward the concentrators 160 and SiPMs 150. The glass plate 140 is disposed on the detection side 134 of the continuous NaI crystal 130.

It may be noted that NaI is a hydroscopic material. As such, to prevent the absorption of moisture that may affect performance, in various embodiments the continuous NaI crystal 130 is disposed within a sealed case 136. Generally, the sealed case 136 is configured to seal out moisture from the continuous NaI crystal. The sealed case 136 in various embodiments is transparent or substantially transparent to radiation emitted from the object 102 (but not to the light emitted by NaI or room light. Further, a light reflector 138 is interposed between the sealed case and the continuous NaI crystal 130. The light reflector 138 is configured to redirect light headed toward the reception side 132 and/or sides along the thickness of the continuous NaI crystal toward the detection side 134. Such redirection provides for more efficient recovery or detection of light produced by the continuous NaI crystal 130. In the illustrated embodiment, the light reflector 138 extends along and covers the reception side 132 along with sides of the continuous NaI crystal 130 along the thickness of the continuous NaI crystal 130. In various embodiments, the light reflector 138 reflects light produced by the continuous NaI crystal 130, but is transparent or substantially transparent to radiation emitted by the object 102. An additional reflector 142 may be placed along the sides of the glass plate 140. The depicted glass plate 140 (as well as the depicted concentrators 160) is configured to allow light from the crystal 130 to pass through toward the SiPMs, and accordingly is made of a material or materials that allow sufficient passage of light to the SiPMs.

Figure 2:
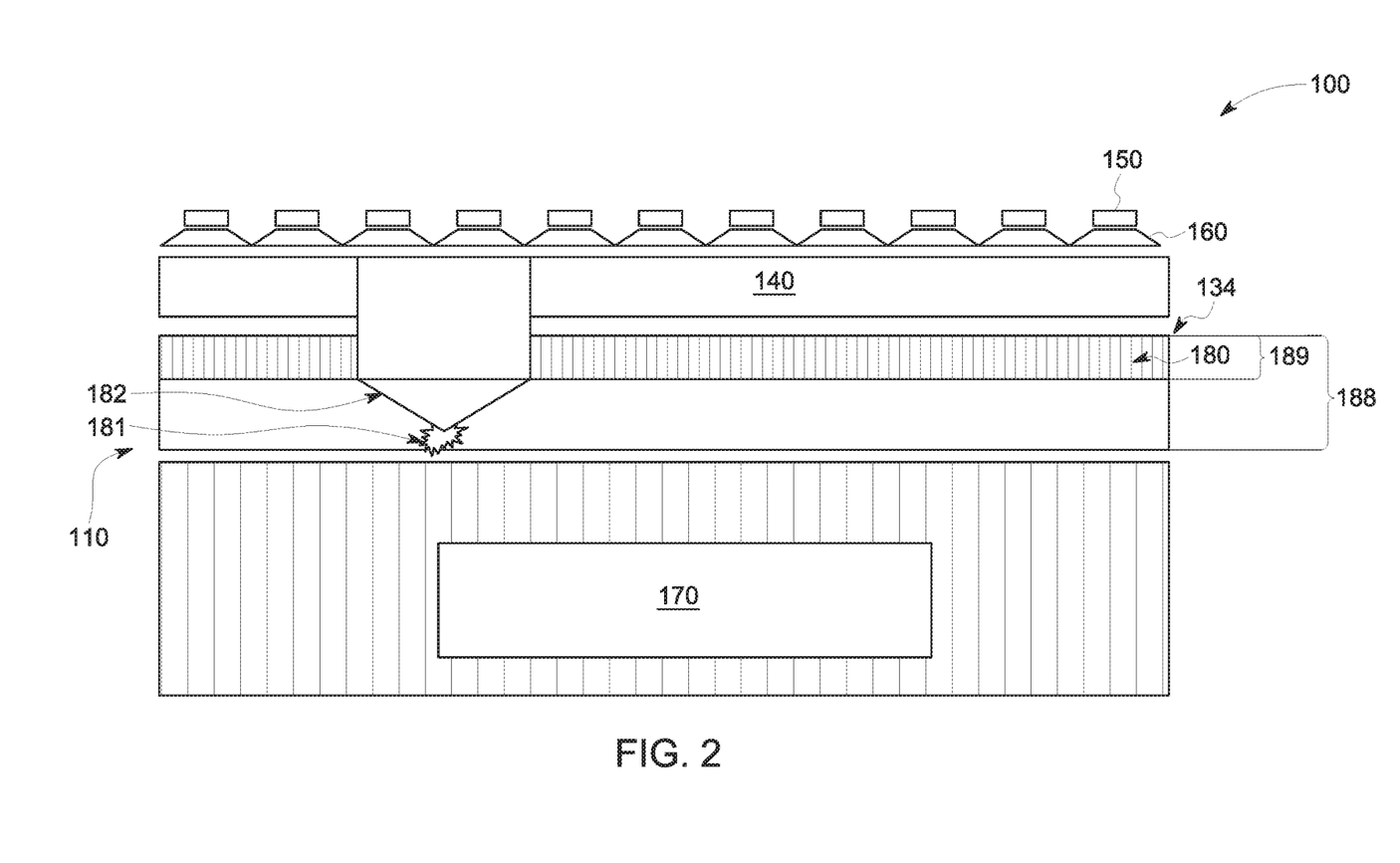
FIG. 2 illustrates a side schematic view of a continuous crystal that includes grooves according to an embodiment.

In various embodiments, the continuous NaI crystal 130 comprises grooves that extend partially into the continuous NaI crystal 130. It may be noted that, as used herein, the term extend partially into may be understood to mean grooves that extend from a given surface but not completely through the NaI crystal 130, thereby allowing the NaI crystal to remain continuous or non-pixelated. FIG. 2 illustrates a side schematic exploded view of an embodiment in which the continuous NaI crystal 130 includes grooves 180. In the embodiment shown in FIG. 2, the grooves 180 extend perpendicularly into the continuous NaI crystal 130 from the detection side 134. It may be noted that perpendicularly as used herein need not necessarily be exactly or perfectly perpendicular, but can include examples that are slightly or insubstantially off from perpendicular, for example due to manufacturing capabilities or tolerances. Generally, the grooves 180 act to limit the spread or distribution of light 182 within the continuous NaI crystal 130, thereby reducing the overall number of SiPMs that receive light corresponding to a given gamma ray impact 181, and/or helping to reduce noise. Alternatively or additionally, grooves 180 may also extend into the continuous NaI crystal 130 from the reception side 132. As noted herein, the grooves 180 extend partially into the continuous NaI crystal 130, but not all the way through. For example, in the illustrated embodiment, the grooves 180 extend a distance 189 down from the reception side 134, with the distance 189 less than one-half of the thickness 188 of the continuous NaI crystal 130. The thickness 188, for example, may be about 9.5 millimeters in some embodiments. In various embodiments, the notches 180 may be as thin as practicable.

Figure 3:
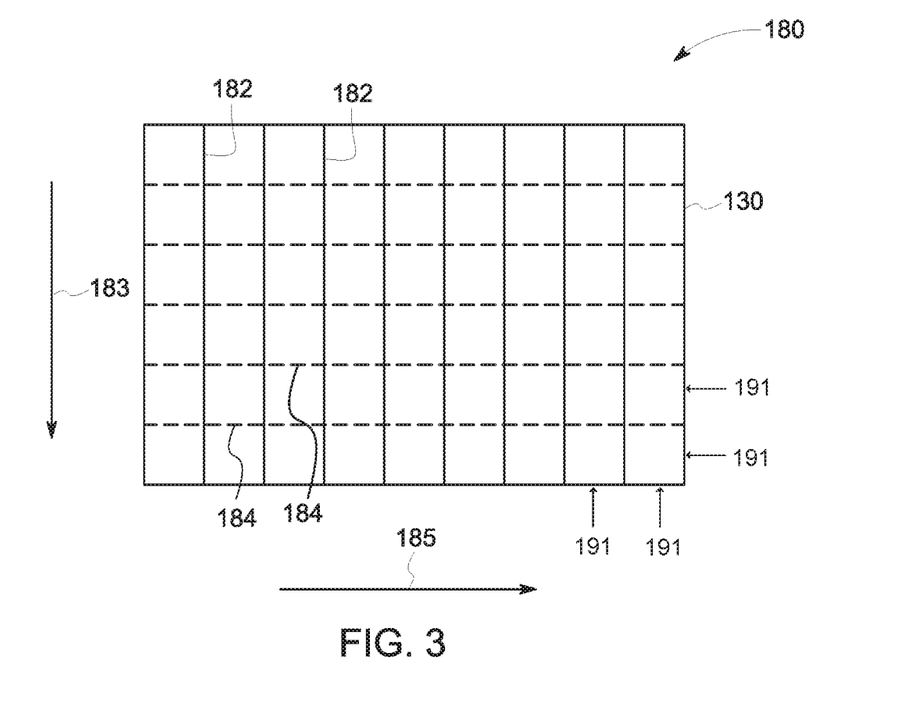
FIG. 3 illustrates a top view of a continuous crystal according to an embodiment.

In some embodiments, a grid of grooves or notches may be employed to help limit the spread of light in two dimensions within a corresponding crystal. For example, FIG. 3 illustrates a top view (looking toward the detection side 134 into which the grooves 180 are cut) of the continuous NaI crystal 130 in accordance with various embodiments. As seen in FIG. 3, the grooves 180 include a first set 182 of grooves 180 (indicated with solid lines) extending along a first direction 183, and a second set 184 of grooves 180 (indicated with dashed lines) extending along a second direction 185. In the illustrated embodiment, the first direction 183 and the second direction 185 are oriented perpendicularly with respect to each other. Gaps 191 separate the rows of grooves 180 from each other. (It may be noted that the gaps 191 in FIG. 3 are depicted as being relatively wide for clarity of illustration, but that the gaps 191 may be quite narrow (e.g., as narrow as practicable) in various embodiments.) In some other embodiments, the size or width of the gaps 191 between grooves may vary and/or the depth of grooves may vary, for example, near to the edge of NaI plate, in order to improve spatial resolution.

Figure 4:
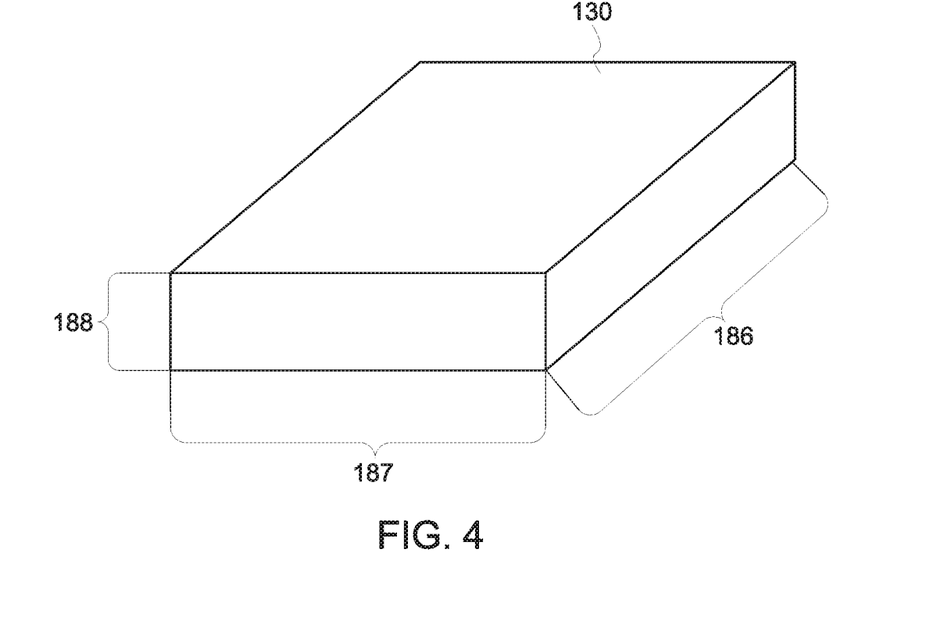
FIG. 4 depicts a perspective view of a continuous crystal in accordance with an embodiment.

It may be noted that the continuous NaI crystal 130 may be substantially larger than crystals used in other imaging applications. For example, a crystal used in connection with PET imaging may be about 6 millimeters×6 millimeters×30 millimeters, or less. FIG. 4 depicts a perspective view of the continuous NaI crystal 130 showing the crystal having a length 186, a width 187, and a thickness 188. The length 186 and/or width 187 may be 40 centimeters or more in various embodiments. For example, in some embodiments (e.g., in certain embodiments that may be used in connection with a general purpose camera), the crystal may be 40×50 centimeters. As another example (e.g., in certain embodiments that may be used in connection with dual head cardiac scanning), the crystal may be 20 centimeters×40 centimeters. As yet another example (e.g., in certain embodiments that may be used in connection with breast imaging), the crystal may be 20 centimeters×20 centimeters. As another example, in some embodiments, the crystal may be 4 centimeters by 28 centimeters. Accordingly, in contrast to conventional PET detectors, a large single crystal may be used to provide a camera having a relatively large field of view.

Returning to FIG. 1, the SiPMs 150 are arranged in the array 152. Generally, the array 152 may be configured as a two-dimensional grid of the SiPMs 150 (e.g., m rows x n columns). The SiPMs are configured to generate electrical signals responsive to the reception of light from the continuous NaI crystal 130, and to provide those signals to the processing unit 120. The SiPMs 150 may be generally larger sized than conventional photodiodes used in connection with imaging (e.g., photodiodes used with pixelated crystals). For example, the SiPMs may have a surface area of about 12 millimeters by 12 millimeters in some embodiments, or, as another example, have a surface area of about one centimeter by one centimeter. Generally, SiPMs have almost two times better photon detection efficiency and enables more compact detector structure compared to traditional PMTs.

It may be noted that in the illustrated embodiment, the total area of SiPM surface (i.e., the sum of the surface area of all of the SiPMs 150) is substantially less than the total area of the detection side 134 of the continuous NaI crystal 130. Accordingly, the number of SiPMs 150 is reduced. In order to provide a corresponding SiPM 150 for every portion of the detection side 134 of the continuous NaI crystal 130 while allowing fewer SiPM 150 to be used, light concentrators 160 are employed to direct light from a larger area along the surface of the continuous NaI crystal 130 to the relatively smaller area of a corresponding SiPM 150. In various embodiments, the configuration does not reduce photon detection efficiency compared to PMTs since SiPM may have two times or higher photon detection efficiency.

In the depicted embodiment, the concentrators 160 are arranged in an array 162 that corresponds to the array 152 of SiPMs 150 (e.g., m rows×n columns in 1:1 correspondence with m rows×n columns of the array 152). For example, in the illustrated embodiment, there is a 1:1 correspondence between concentrators 160 and SiPMs 150, with each concentrator associated with and configured to funnel light towards a particular SiPM 150. The array 162 of concentrators 160 is interposed between the array 152 of SiPMs 150 and the glass plate 140. For example, each concentrator 160 may be configured as a glass or plastic shape configured to funnel light to a corresponding SiPM 150, with the concentrators 160 glued or otherwise adhered or fixed to the glass plate 140. Compared to traditional photomultipliers, the concentrators 160 of various embodiments provide better light collection (e.g., through the reduction or elimination of dead space), accordingly improving both spatial resolution and energy resolution.

Figure 5:
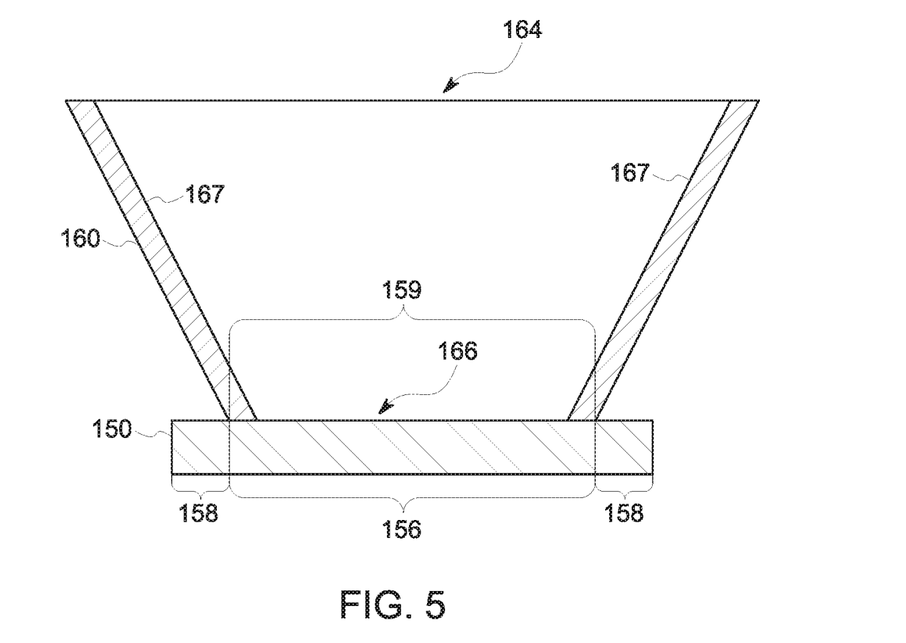
FIG. 5 provides a schematic cross-sectional view of a concentrator and corresponding SiPM in accordance with an embodiment.

Generally, the concentrators 160 are configured to funnel light to a corresponding SiPM 150. FIG. 5 provides a schematic cross-sectional view of a concentrator 160 and corresponding SiPM 150 in accordance with various embodiments. As seen in FIG. 5, the depicted concentrator 160 includes a reception side opening 164 and a detection side opening 166. The reception side opening 164 is disposed proximate (e.g., in contact with) the glass plate 140 (see FIG. 1), and the detection side opening 166 is disposed proximate to the corresponding SiPM 150. The detection side opening 166 is smaller than the reception side opening 164. Accordingly, light received via the reception side opening 164 is funneled to a smaller area and delivered to the SiPM 150 via the detection side opening 166. As seen in FIG. 5, the depicted concentrator 160 has a truncated pyramid shape, with its walls 167 sloping linearly from the reception side opening 164 to the detection side opening 166. It may be noted that other sizes and/or shapes of concentrators may be employed in other embodiments.

It may be noted that the SiPMs 150 may have a portion or area (e.g., around the edges of the device) that may be referred to as "dead" or "inactive." Signals are not generated responsive to photon impacts on the dead or inactive regions, and are only generated responsive to photon impacts on the active portions or areas of the SiPMs 150. In various embodiments, the concentrator 160 is configured to direct light toward active areas and away from inactive or dead areas of a corresponding SiPM. For example, in the embodiment depicted in FIG. 5, the SiPM has an active area 156 and an inactive area 158, with a boundary 159 defined between the active area 156 and the inactive area 158. The detection side opening 166 of the depicted concentrator 160 is disposed within the active portion within the boundary 159. Accordingly, light from the concentrator 160 is directed to the active area 156 and not the inactive area 158.

Figure 6:
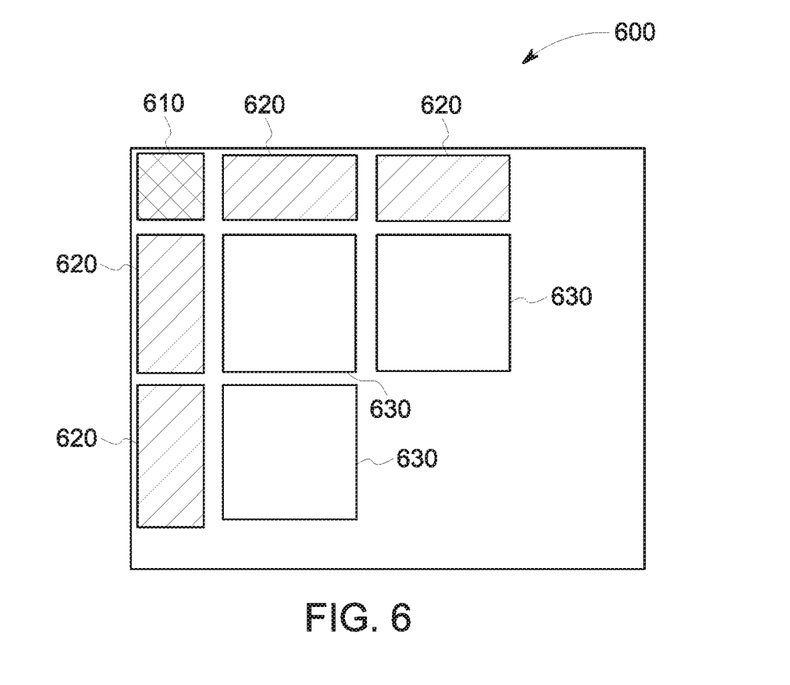
FIG. 6 depicts a top view of a concentrator array having differently sized concentrators, according to an embodiment.

It may also be noted that the array 162 may be uniform in some embodiments, or not uniform in other embodiments. For example, a uniform array may include identically sized concentrators 160 having square shaped openings disposed at a consistent pitch with respect to each other in one or more dimensions. However, a non-uniform array may have different sized and/or differently spaced concentrators. For example, FIG. 6 depicts a top view of a concentrator array 600 having differently sized concentrators. For example, the concentrator array 600 includes a corner concentrator 610 configured as a relatively small square, edge concentrators 620 configured as oblong rectangles, and interior concentrators 630 configured as relatively large squares. Use of unevenly spaced, skewed, or differently sized concentrators in various embodiments allows for tailoring the array 162 of concentrators 160 for particular crystal geometries. In various embodiments, use of unevenly spaced, skewed, or differently sized concentrators helps to reduce edge dead space and improve resolution at edges of a crystal.

With continued reference to FIG. 1, the collimator 170 is configured to control or limit the angle at which photons impact the imaging detector 110. The collimator 170 is disposed on the reception side 132 of the continuous NaI crystal 130. Generally, the collimator 170 includes openings separated by septa through which radiation emitted from the object 102 passes before impacting the continuous NaI crystal 130. The size of the openings, along with the length of the septa, defines the range of angular approaches at which impact with the continuous NaI crystal 130 is allowed. It may be noted that, as the continuous NaI crystal 130 is not pixelated, a non-registered collimator may be employed, reducing cost.

As discussed herein, the processing unit 120 is configured to acquire imaging information from the imaging detector 110 and to reconstruct an image of the object 102 using the acquired imaging information. In the illustrated embodiment, the processing unit 120 is coupled to the SiPMs 150 via a printed circuit board (PCB) 121 to which the SiPMs 150 are mounted. Signals generated by the SiPMs 150 responsive to light photon impacts are provided to the processing unit 120, and used by the processing unit 120 to determine the location of corresponding radiation emitted from the object 102, and to reconstruct an image of the object 102. Generally, the number of photon impacts associated with various portions of the object 102 may be counted and used to reconstruct an image. For example, a given emission from the object 102 may result in an impact with the continuous NaI crystal 130 that results in light photons being produced and in turn impacting multiple SiPMs 150. The processing unit 120 may analyze the number of light photons received by each of a number of SiPMs and determine a center of gravity or other location corresponding to the received light photons.

In various embodiments the processing unit 120 includes processing circuitry configured to perform one or more tasks, functions, or steps discussed herein. It may be noted that "processing unit" as used herein is not intended to necessarily be limited to a single processor or computer. For example, the processing unit 120 may include multiple processors, FPGA's, ASIC's and/or computers, which may be integrated in a common housing or unit, or which may distributed among various units or housings (e.g., one or more aspects of the processing unit 120 may be disposed onboard one or more detector units, and one or more aspects of the processing unit 120 may be disposed in a separate physical unit or housing). In the illustrated embodiment, the processing unit 120 includes a memory 122. Generally, the various aspects of the processing unit 120 act individually or cooperatively with other aspects to perform one or more aspects of the methods, steps, or processes discussed herein, for example to reconstruct an image. Further, the process flows and/or flowcharts discussed herein (or aspects thereof) may represent one or more sets of instructions that are stored in the memory 122 for direction of operations of the imaging system 100.

Figure 9:
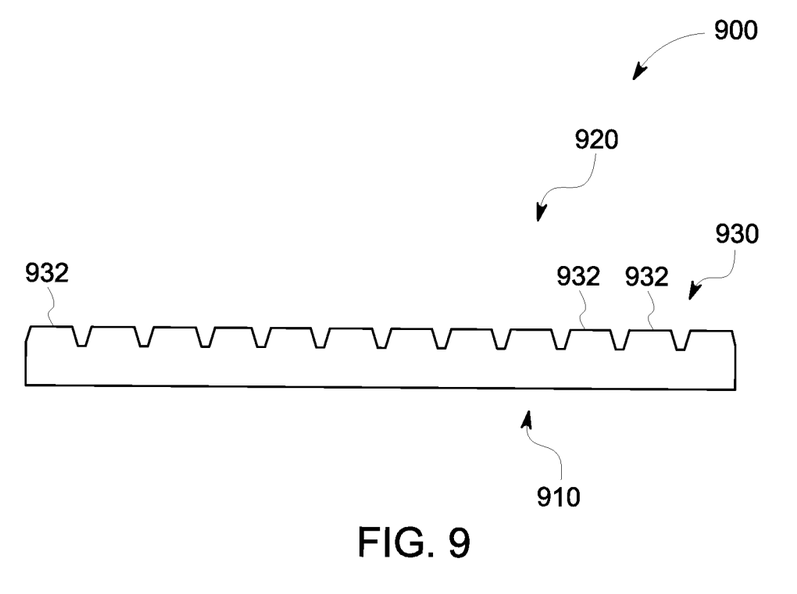
FIG. 9 provides a side view of a glass plate with an integrated concentrator array, according to an embodiment.

It may be noted that, in some embodiments, the array of concentrators is integrally formed with the glass plate. For example, FIG. 9 illustrates a side view of a glass plate 900. The glass plate 900 includes a first side 910, and a second side 920. The first side 910 is configured to be oriented toward a crystal, and the second side 920 is configured to be oriented toward SiPMs. An array 930 of concentrators 932 extend from the glass plate 900 on the second side 920. In the depicted embodiment, the array 930 of concentrators 932 is an integrated part of the glass plate 900, with the flat portion of the glass plate as well as the concentrators 932 formed from a single piece of glass.

Figure 7:
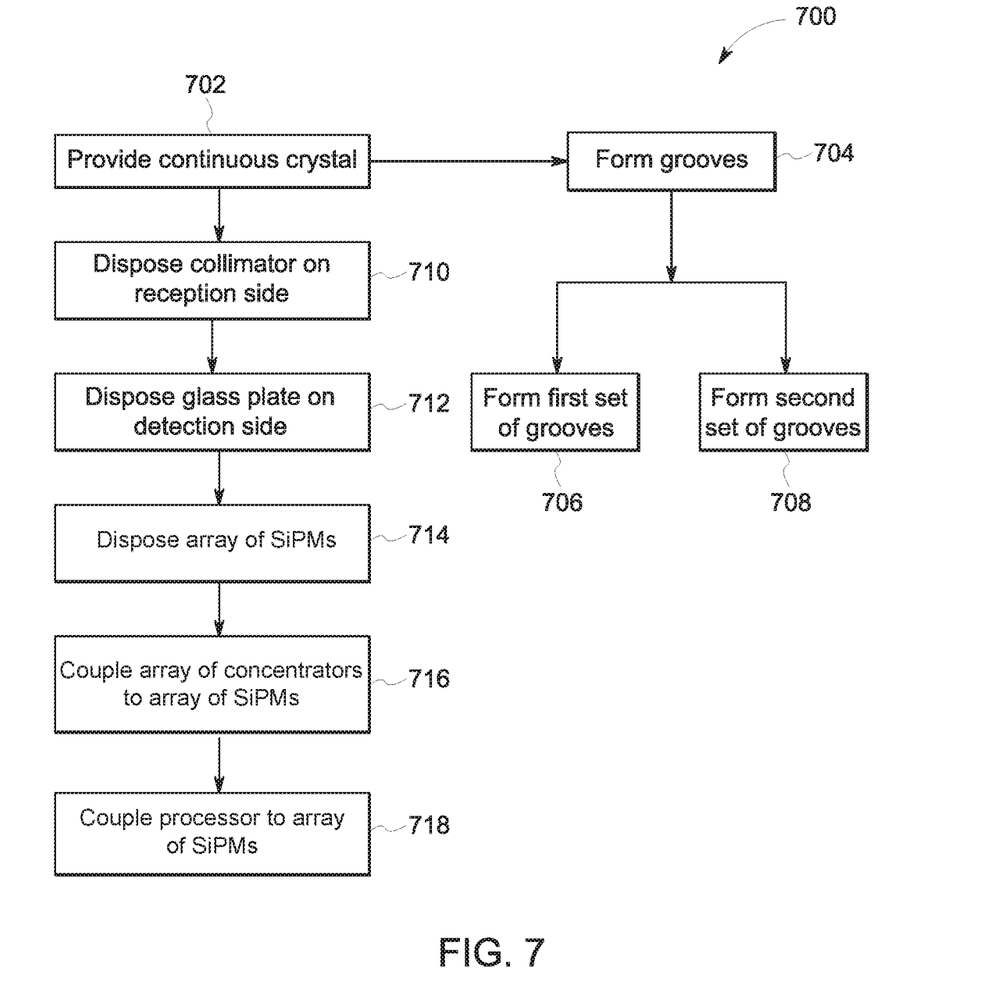
FIG. 7 shows a flowchart of a method, according to an embodiment.

FIG. 7 provides a flowchart of a method 700 for providing an imaging detector and/or detector system in accordance with various embodiments. The method 700 (or aspects thereof), for example, may employ or be performed by structures or aspects of various embodiments (e.g., systems and/or methods and/or process flows) discussed herein. In various embodiments, certain steps may be omitted or added, certain steps may be combined, certain steps may be performed concurrently, certain steps may be split into multiple steps, certain steps may be performed in a different order, or certain steps or series of steps may be re-performed in an iterative fashion.

At 702, a continuous NaI crystal (e.g., continuous NaI crystal 130) is provided. As used herein, a continuous crystal may be understood as a non-pixelated crystal. The continuous NaI crystal defines a reception side and a detection side. The reception side is oriented toward an object being imaged that is emitting radiation, and the reception side may include a reception surface that receives emitted radiation. The continuous NaI crystal emits light photons in response to the received radiation. The detection side is opposite the reception side, or oriented away from the object being imaged, or oriented toward SiPMs that receive light generated by the NaI crystal responsive to received radiation. It may be noted that, in some embodiments, for example to protect the crystal from moisture, the continuous NaI crystal may be disposed in a sealed case. In various embodiments, a light reflector may be interposed between the sealed case and the continuous NaI crystal.

In some embodiments, before sealing the NaI crystal in the case, grooves may be formed to help control light distribution within the crystal. The grooves may be formed, for example, by cutting into the crystal with as thin a blade as practical. The grooves may extend, in some embodiments, less than halfway into the total thickness of the crystal. For example, in the depicted embodiment, at 704, grooves are formed that extend partially into the continuous NaI crystal. It may be noted that the grooves may extend into one or both of the reception side and/or the detection side. For example, in some embodiments, the grooves extend perpendicularly into the continuous NaI crystal from the detection side. Grooves may be formed in more than one direction in various embodiments. For example, in the illustrated embodiment, at 706, a first set of grooves are formed extending along a first direction. At 708, a second set of grooves are formed extending along a second direction. The first direction is perpendicular to the second direction. In some embodiments, gaps between grooves and depth may vary, depending on location, to help control the distribution of scintillation light and to accordingly improve spatial resolution.

At 710, a collimator (e.g., collimator 170) is disposed on the reception side of the continuous NaI crystal. As the crystal is non-pixelated, an un-registered collimator may be used. At 712, a glass plate is disposed on the detection side of the continuous NaI crystal (e.g., opposite the collimator).

At 714, an array (e.g., array 152) of SiPMs (e.g., SiPMs 150) are disposed oriented toward the detection side of the continuous NaI crystal, such that light photons emitted from the detection side of the continuous NaI crystal are directed toward the array of SiPMs. The glass plate is interposed between the detection side of the continuous NaI crystal and the array of SiPMs.

At 716, an array (e.g., array 162) of concentrators (e.g., concentrators 160) is coupled to the array of SiPMs. The array of concentrators is interposed between the glass plate and the array of SiPMs, with each concentrator configured to funnel light toward a particular SiPM. For example, the concentrators may be glued or otherwise adhered to the glass plate and then affixed to the corresponding SiPMs. Each concentrator has a reception side opening that is larger than a detection side opening, with the detection side opening disposed proximate to a corresponding SiPM. In some embodiments, the concentrators are connected or coupled to the SiPMs such that the detection side opening of each concentrator is disposed within a boundary defined by an active area of the corresponding SiPM. It may be noted that all or a portion of step 716 may take place before all or a portion of step 714 in various embodiments. For example, the array of concentrators may first be disposed relative to the detection side of the continuous NaI crystal (e.g., glued or otherwise adhered in a grid or other predetermined arrangement to the glass plate) before the array of SiPMs are positioned and/or secured in place. As another example, the array of concentrators may first be adhered to the glass plate before the glass plate is coupled or joined to the continuous NaI crystal.

At 718, at least one processor is coupled to the array of SiPMs. For example, the SiPMs may be mounted to a PCB that is coupled to the at least one processor. Accordingly, the at least one processor may receive signals from the SiPMs (e.g., signals corresponding to light photons impacting the SiPMs.

Figure 8:
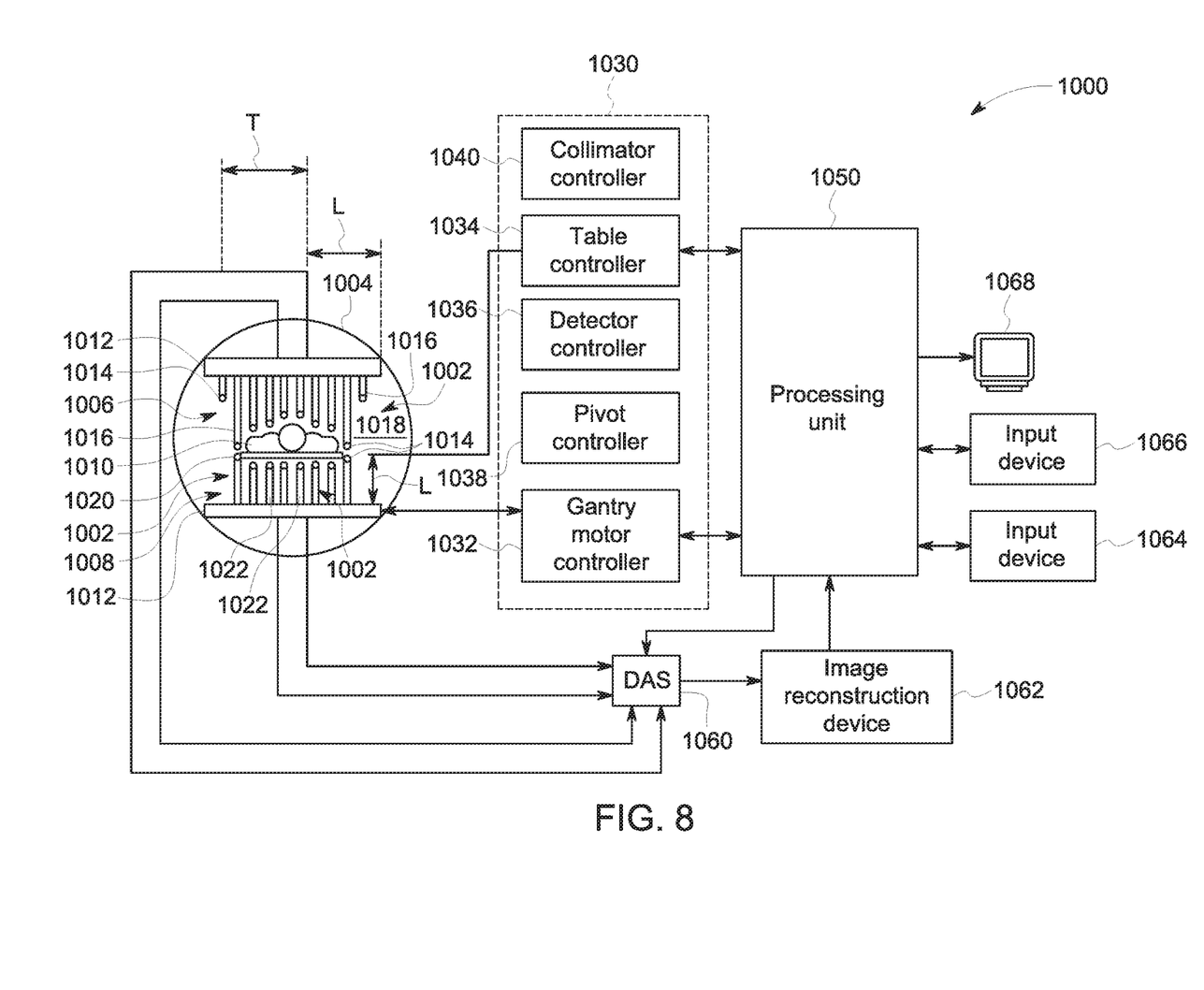
FIG. 8 shows a schematic view of an imaging system, according to an embodiment.

Embodiments described herein may be implemented in medical imaging systems. Various methods and/or systems (and/or aspects thereof) described herein may be implemented using a medical imaging system. For example, FIG. 8 is a schematic illustration of a NM imaging system 1000 having a plurality of imaging detector head assemblies mounted on a gantry (which may be mounted, for example, in rows, in an iris shape, or other configurations, such as a configuration in which the movable detector carriers 1016 are aligned radially toward the patient-body 1010). It should be noted that the arrangement of FIG. 8 is provided by way of example for illustrative purposes, and that other arrangements (e.g., detector arrangements) may be employed in various embodiments. In the illustrated example, a plurality of imaging detectors 1002 are mounted to a gantry 1004. In the illustrated embodiment, the imaging detectors 1002 are configured as two separate detector arrays 1006 and 1008 coupled to the gantry 1004 above and below a subject 1010 (e.g., a patient), as viewed in FIG. 8. The detector arrays 1006 and 1008 may be coupled directly to the gantry 1004, or may be coupled via support members 1012 to the gantry 1004 to allow movement of the entire arrays 1006 and/or 1008 relative to the gantry 1004 (e.g., transverse translating movement in the left or right direction as viewed by arrow T in FIG. 8). Additionally, each of the imaging detectors 1002 includes a detector unit 1014, at least some of which are mounted to a movable detector carrier 1016 (e.g., a support arm or actuator that may be driven by a motor to cause movement thereof) that extends from the gantry 1004. In some embodiments, the detector carriers 1016 allow movement of the detector units 1014 towards and away from the subject 1010, such as linearly. Thus, in the illustrated embodiment the detector arrays 1006 and 1008 are mounted in parallel above and below the subject 1010 and allow linear movement of the detector units 1014 in one direction (indicated by the arrow L), illustrated as perpendicular to the support member 1012 (that are coupled generally horizontally on the gantry 1004). However, other configurations and orientations are possible as described herein. It should be noted that the movable detector carrier 1016 may be any type of support that allows movement of the detector units 1014 relative to the support member 1012 and/or gantry 1004, which in various embodiments allows the detector units 1014 to move linearly towards and away from the support member 1012.

It should be understood that the imaging detectors 1002 may be different sizes and/or shapes with respect to each other, such as square, rectangular, circular or other shape. An actual field of view (FOV) of each of the imaging detectors 1002 may be directly proportional to the size and shape of the respective imaging detector.

The gantry 1004 may be formed with an aperture 1018 (e.g., opening or bore) therethrough as illustrated. A patient table 1020, such as a patient bed, is configured with a support mechanism (not shown) to support and carry the subject 1010 in one or more of a plurality of viewing positions within the aperture 1018 and relative to the imaging detectors 1002. Alternatively, the gantry 1004 may comprise a plurality of gantry segments (not shown), each of which may independently move a support member 1012 or one or more of the imaging detectors 1002.

The gantry 1004 may also be configured in other shapes, such as a "C", "H" and "L", for example, and may be rotatable about the subject 1010. For example, the gantry 1004 may be formed as a closed ring or circle, or as an open arc or arch which allows the subject 1010 to be easily accessed while imaging and facilitates loading and unloading of the subject 1010, as well as reducing claustrophobia in some subjects 1010.

Additional imaging detectors (not shown) may be positioned to form rows of detector arrays or an arc or ring around the subject 1010. By positioning multiple imaging detectors 1002 at multiple positions with respect to the subject 1010, such as along an imaging axis (e.g., head to toe direction of the subject 1010) image data specific for a larger FOV may be acquired more quickly.

Each of the imaging detectors 1002 has a radiation detection face, which is directed towards the subject 1010 or a region of interest within the subject.

A controller unit 1030 may control the movement and positioning of the patient table 1020, imaging detectors 1002 (which may be configured as one or more arms), gantry 1004 and/or the collimators 1022 (that move with the imaging detectors 1002 in various embodiments, being coupled thereto). A range of motion before or during an acquisition, or between different image acquisitions, is set to maintain the actual FOV of each of the imaging detectors 1002 directed, for example, towards or "aimed at" a particular area or region of the subject 1010 or along the entire subject 1010. The motion may be a combined or complex motion in multiple directions simultaneously, concurrently, or sequentially.

The controller unit 1030 may have a gantry motor controller 1032, table controller 1034, detector controller 1036, pivot controller 1038, and collimator controller 1040. The controllers 1030, 1032, 1034, 1036, 1038, 1040 may be automatically commanded by a processing unit 1050, manually controlled by an operator, or a combination thereof. The gantry motor controller 1032 may move the imaging detectors 1002 with respect to the subject 1010, for example, individually, in segments or subsets, or simultaneously in a fixed relationship to one another. For example, in some embodiments, the gantry controller 1032 may cause the imaging detectors 1002 and/or support members 1012 to move relative to or rotate about the subject 1010, which may include motion of less than or up to 180 degrees (or more).

The table controller 1034 may move the patient table 1020 to position the subject 1010 relative to the imaging detectors 1002. The patient table 1020 may be moved in up-down directions, in-out directions, and right-left directions, for example. The detector controller 1036 may control movement of each of the imaging detectors 1002 to move together as a group or individually. The detector controller 1036 also may control movement of the imaging detectors 1002 in some embodiments to move closer to and farther from a surface of the subject 1010, such as by controlling translating movement of the detector carriers 1016 linearly towards or away from the subject 1010 (e.g., sliding or telescoping movement). Optionally, the detector controller 1036 may control movement of the detector carriers 1016 to allow movement of the detector array 1006 or 1008. For example, the detector controller 1036 may control lateral movement of the detector carriers 1016 illustrated by the T arrow (and shown as left and right as viewed in FIG. 10). In various embodiments, the detector controller 1036 may control the detector carriers 1016 or the support members 1012 to move in different lateral directions. Detector controller 1036 may control the swiveling motion of detectors 1002 together with their collimators 1022. In some embodiments, detectors 1002 and collimators 1022 may swivel or rotate around an axis.

The pivot controller 1038 may control pivoting or rotating movement of the detector units 1014 at ends of the detector carriers 1016 and/or pivoting or rotating movement of the detector carrier 1016. For example, one or more of the detector units 1014 or detector carriers 1016 may be rotated about at least one axis to view the subject 1010 from a plurality of angular orientations to acquire, for example, 3D image data in a 3D SPECT or 3D imaging mode of operation. The collimator controller 1040 may adjust a position of an adjustable collimator, such as a collimator with adjustable strips (or vanes) or adjustable pinhole(s).

It should be noted that motion of one or more imaging detectors 1002 may be in directions other than strictly axially or radially, and motions in several motion directions may be used in various embodiment. Therefore, the term "motion controller" may be used to indicate a collective name for all motion controllers. It should be noted that the various controllers may be combined, for example, the detector controller 1036 and pivot controller 1038 may be combined to provide the different movements described herein.

Prior to acquiring an image of the subject 1010 or a portion of the subject 1010, the imaging detectors 1002, gantry 1004, patient table 1020 and/or collimators 1022 may be adjusted, such as to first or initial imaging positions, as well as subsequent imaging positions. The imaging detectors 1002 may each be positioned to image a portion of the subject 1010. Alternatively, for example in a case of a small size subject 1010, one or more of the imaging detectors 1002 may not be used to acquire data, such as the imaging detectors 1002 at ends of the detector arrays 1006 and 1008, which as illustrated in FIG. 8 are in a retracted position away from the subject 1010. Positioning may be accomplished manually by the operator and/or automatically, which may include using, for example, image information such as other images acquired before the current acquisition, such as by another imaging modality such as X-ray Computed Tomography (CT), MRI, X-Ray, PET or ultrasound. In some embodiments, the additional information for positioning, such as the other images, may be acquired by the same system, such as in a hybrid system (e.g., a SPECT/CT system). Additionally, the detector units 1014 may be configured to acquire non-NM data, such as x-ray CT data. In some embodiments, a multi-modality imaging system may be provided, for example, to allow performing NM or SPECT imaging, as well as x-ray CT imaging, which may include a dual-modality or gantry design as described in more detail herein.

After the imaging detectors 1002, gantry 1004, patient table 1020, and/or collimators 1022 are positioned, one or more images, such as three-dimensional (3D) SPECT images are acquired using one or more of the imaging detectors 1002, which may include using a combined motion that reduces or minimizes spacing between detector units 1014. The image data acquired by each imaging detector 1002 may be combined and reconstructed into a composite image or 3D images in various embodiments.

In one embodiment, at least one of detector arrays 1006 and/or 1008, gantry 1004, patient table 1020, and/or collimators 1022 are moved after being initially positioned, which includes individual movement of one or more of the detector units 1014 (e.g., combined lateral and pivoting movement) together with the swiveling motion of detectors 1002. For example, at least one of detector arrays 1006 and/or 1008 may be moved laterally while pivoted. Thus, in various embodiments, a plurality of small sized detectors, such as the detector units 1014 may be used for 3D imaging, such as when moving or sweeping the detector units 1014 in combination with other movements.

In various embodiments, a data acquisition system (DAS) 1060 receives electrical signal data produced by the imaging detectors 1002 and converts this data into digital signals for subsequent processing. However, in various embodiments, digital signals are generated by the imaging detectors 1002. An image reconstruction device 1062 (which may be a processing device or computer) and a data storage device 1064 may be provided in addition to the processing unit 1050. It should be noted that one or more functions related to one or more of data acquisition, motion control, data processing and image reconstruction may be accomplished through hardware, software and/or by shared processing resources, which may be located within or near the imaging system 1000, or may be located remotely. Additionally, a user input device 1066 may be provided to receive user inputs (e.g., control commands), as well as a display 1068 for displaying images. DAS 1060 receives the acquired images from detectors 1002 together with the corresponding lateral, vertical, rotational and swiveling coordinates of gantry 1004, support members 1012, detector units 1014, detector carriers 1016, and detectors 1002 for accurate reconstruction of an image including 3D images and their slices.

It should be noted that the particular arrangement of components (e.g., the number, types, placement, or the like) of the illustrated embodiments may be modified in various alternate embodiments, and/or one or more aspects of illustrated embodiments may be combined with one or more aspects of other illustrated embodiments. For example, in various embodiments, different numbers of a given module or unit may be employed, a different type or types of a given module or unit may be employed, a number of modules or units (or aspects thereof) may be combined, a given module or unit may be divided into plural modules (or sub-modules) or units (or sub-units), one or more aspects of one or more modules may be shared between modules, a given module or unit may be added, or a given module or unit may be omitted.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless and until specifically programmed or structurally modified to perform the task or operation.

As used herein, the term "computer," "processor," or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer," "processor," or "module."

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" may include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, the embodiments are by no means limiting and are exemplary embodiments. Many other embodiments will be apparent to those of skill in the art upon reviewing the above description. The scope of the various embodiments should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. An imaging detector comprising:
a continuous NaI crystal defining a reception side and a detection side;
a glass plate disposed on the detection side of the continuous NaI crystal;
an array of SiPMs, the glass plate interposed between the detection side of the continuous NaI crystal and the array of SiPMs; and
an array of concentrators corresponding to the array of SiPMs and interposed between the array of SiPMs and the glass plate, each concentrator having a reception side opening that is larger than a detection side opening, with the detection side opening disposed proximate to a corresponding SiPM.

2. The imaging detector of claim 1, wherein the continuous NaI crystal is disposed in a sealed case, the imaging detector comprising a light reflector interposed between the sealed case and the continuous NaI crystal.

3. The imaging detector of claim 1, wherein the continuous NaI crystal comprises grooves extending partially into the continuous NaI crystal.

4. The imaging detector of claim 3, wherein the grooves extend perpendicularly into the NaI crystal from the detection side of the continuous NaI crystal.

5. The imaging detector of claim 3, wherein the grooves comprise a first set of grooves extending along a first direction and a second set of grooves extending along a second direction, the first direction oriented perpendicularly to the second direction.

6. The imaging detector of claim 3, wherein gaps between grooves and the depth of grooves vary depending on its location.

7. The imaging detector of claim 1, wherein the continuous NaI crystal has a length of at least 28 centimeters and a width of at least 4 centimeters.

8. The imaging detector of claim 1, wherein the concentrators comprises differently sized concentrators.

9. The imaging detector of claim 1, wherein the detection side opening of each concentrator is disposed within a boundary defined by an active area of the corresponding SiPM.

10. The imaging detector of claim 1, wherein the array of concentrators are integrally formed with the glass plate.

11. An imaging system comprising:
a continuous NaI crystal defining a reception side and a detection side;
a non-registered collimator disposed on the reception side of the continuous NaI crystal;
a glass plate disposed on the detection side of the continuous NaI crystal;
an array of SiPMs, the glass plate interposed between the detection side of the continuous NaI crystal and the array of SiPMs;
an array of concentrators corresponding to the array of SiPMs and interposed between the array of SiPMs and the glass plate, each concentrator having a reception side opening that is larger than a detection side opening, with the detection side opening disposed proximate to a corresponding SiPM; and
at least one processor operably coupled to the array of SiPMs, the at least one processor configured to acquire imaging information with the array of SiPMs and reconstruct an image using the imaging information.

12. The imaging system of claim 11, wherein the continuous NaI crystal comprises grooves extending partially into the continuous NaI crystal.

13. The imaging system of claim 12, wherein the grooves extend perpendicularly into the NaI crystal from the detection side of the continuous NaI crystal.

14. The imaging system of claim 12, wherein the grooves comprise a first set of grooves and a second set of grooves, the first set of grooves oriented perpendicularly to the second set of grooves.

15. The imaging system of claim 11, wherein the array of concentrators are integrally formed with the glass plate.

16. A method comprising:
providing a continuous NaI crystal defining a reception side and a detection side;
disposing a glass plate on the detection side of the continuous NaI crystal;
disposing an array of SiPMs with the glass plate interposed between the detection side of the continuous NaI crystal and the array of SiPMs; and
coupling an array of concentrators to the array of SiPMs, the array of concentrators interposed between the array of SiPMs and the glass plate, each concentrator having a reception side opening that is larger than a detection side opening, with the detection side opening disposed proximate to a corresponding SiPM.

17. The method of claim 16, wherein providing the continuous NaI crystal comprises disposing the continuous NaI crystal in a sealed case, with a light reflector interposed between the sealed ease and the continuous NaI crystal.

18. The method of claim 16, further comprising forming grooves extending partially into the continuous NaI crystal.

19. The method of claim 18, wherein the grooves extend perpendicularly into the NaI crystal from the detection side of the continuous NaI crystal.

20. The method of claim 18, wherein forming the rooves comprises forming a first set of grooves extending along a first direction, and forming a second set of grooves extending along a second direction, the first direction perpendicular to the second direction.

* * * * *